United States Patent [19]
Ichihashi et al.

[11] Patent Number: 5,354,859
[45] Date of Patent: * Oct. 11, 1994

[54] ε-CAPROLACTAM

[75] Inventors: Hiroshi Ichihashi, Shiga; Masaru Kitamura, Osaka; Hiroshi Kajikuri, Osaka; Eiji Tasaka, Osaka, all of Japan

[73] Assignee: Sumitomo Chemical Company Limited, Osaka, Japan

[*] Notice: The portion of the term of this patent subsequent to May 18, 2010 has been disclaimed.

[21] Appl. No.: 981,476

[22] Filed: Nov. 25, 1992

[30] Foreign Application Priority Data

Nov. 27, 1991 [JP] Japan ................. 3-312492
Nov. 27, 1991 [JP] Japan ................. 3-312493

[51] Int. Cl.$^5$ .................................. C07D 201/04
[52] U.S. Cl. ............................. 540/536; 540/535
[58] Field of Search .............. 540/533, 536, 535

[56] References Cited

U.S. PATENT DOCUMENTS

| | | | |
|---|---|---|---|
| 2,234,566 | 3/1941 | Lazier et al. | 540/536 |
| 4,968,793 | 11/1990 | Kitamura | 540/536 |
| 5,212,302 | 5/1993 | Kitamura et al. | 540/536 |

FOREIGN PATENT DOCUMENTS

| | | | |
|---|---|---|---|
| 0234088 | 9/1987 | European Pat. Off. | 540/536 |
| 0236092 | 9/1987 | European Pat. Off. | 540/536 |
| 0242960 | 10/1987 | European Pat. Off. | 540/536 |
| 0369364 | 5/1990 | European Pat. Off. | 540/536 |
| 0380364 | 8/1990 | European Pat. Off. | 540/536 |
| 0388070 | 9/1990 | European Pat. Off. | 540/536 |
| 0494535 | 7/1992 | European Pat. Off. | 540/536 |
| 1545789 | 10/1969 | Fed. Rep. of Germany | 540/535 |

OTHER PUBLICATIONS

Chemical Abstracts 104: 185769q (1986).
"A Vapor Phase Beckmann Rearrangement over Highly Silicious ZSM-5 with CVD Treatment" (with partial English translation).
The Canadian Journal of Chemical Engineering, vol. 69, Oct., 1991.

*Primary Examiner*—Robert T. Bond
*Attorney, Agent, or Firm*—Cushman, Darby & Cushman

[57] ABSTRACT

ε-Caprolactam is prepared by bringing cyclohexanone oxime into contact in gas phase with solid catalysts such as a zeolite catalyst in the presence of at least one nitrogen-containing compound selected from the group consisting of ammonia, methylamines and ε-caprolactam.

18 Claims, No Drawings

ε-CAPROLACTAM

The present invention relates to a process for producing ε-caprolactam from cyclohexanone oxime using solid catalysts under gas phase reaction conditions.

ε-Caprolactam is an important raw material for nylon and the like.

The inventors have proposed processes for producing ε-caprolactam by rearrangement of cyclohexanone oxime (Beckmann rearrangement) using solid catalysts under gas phase reaction conditions in tile presence of lower alcohols and/or ether compounds (Japanese Patent Kokai Nos. Hei 2-275850 and 2-250866).

The inventors have further conducted intensive research on a rearrangement reaction of cyclohexanone oxime and have found that when the rearrangement reaction is carried out in the presence of specific nitrogen-containing compounds in the reaction system, ε-caprolactam is obtained with a high selectivity and life of the catalysts are greatly prolonged even under such conditions that cyclohexanone oxime reacts with high conversion. As a result, the present invention has been accomplished.

That is, the present invention provides an industrially superior process for producing ε-caprolactam which comprises bringing cyclohexanone oxime into contact in a gas phase with solid catalysts in the presence of at least one nitrogen-containing compound selected from ammonia, methylamines and ε-caprolactam.

The present invention will be explained in detail below.

The solid catalysts used in tile present invention include, for example, silica-alumina and zeolites and in particular, crystalline silica and crystalline metallosilicates are preferred. The crystalline silica used in the present invention comprises substantially silicon and oxygen. The crystalline metallosilicates contain metals in addition to silicon and oxygen, such as those which have a ratio of the number of silicon atom to that of metal atoms (Si/metal atomic ratio) of 5 or higher, preferably at least 500. As examples of the metals, mention may be made of at least one metal selected from Al, Ga, Fe, B, Zn, Cr, Be, Co, La, Ge, Ti, Zr, Hf, V, Ni, Sb, Bi, Cu and Nb. The Si/metal atomic ratio is obtained by usual analytical methods such as atomic absorption spectrometry and X-ray fluorescence analysis. These catalysts are prepared by known processes. The crystalline silica and crystalline metallosilicateshave various crystalline forms and those which belong to pentasil type structure are preferred.

The process of the present invention is characterized in that a specific nitrogen-containing compound is allowed to exist in the reaction system. The nitrogen-containing compounds include at least one compound selected from ammonia, methylamines and ε-caprolactam. Among them, ammonia and methylamines give preferable results. The methylamines include, for example, monomethylamine, dimethylamine and trimethylamine.

Amount of the nitrogen-containing compounds is usually 10 moles or less, preferably 1 mole or less, more preferably 0.001–0.8 mole per mol of cyclohexanone oxime used.

In the present invention, alcohols or ether compounds may be allowed to exist in the reaction system, in order to improve selectivity of the desired product. The alcohols and ether compounds include the compounds represented by the following formula (1).

$$R_1-O-R_2 \quad (1)$$

(wherein $R_1$ represents a lower alkyl group which may be substituted with at least one fluorine atom and $R_2$ represents a hydrogen atom or a lower alkyl or phenyl group which may be substituted with at least one fluorine atom).

Examples of the alcohols are lower alcohols of 6 or less carbon atoms such as methanol, ethanol, n-propanol, isopropanol, n-butanol, sec-butanol, isobutanol, n-amyl alcohol, n-hexanol and 2,2,2-trifluoroethanol. Methanol and ethanol are preferred. The ether compounds are preferably those which have a methyl group or an ethyl group as $R_1$ in the formula (1). Examples are ether compounds of 8 or less carbon atoms such as dimethyl ether, methylethyl ether, diethyl ether, methyl-n-propyl ether, methylisopropyl ether, methyl-tert-butyl ether and anisole. Two or more of alcohols or two or more of ether compounds may be used. Alcohols may also be mixed with ether compounds.

In the reaction system, vapors of compounds inert to the reaction, such as benzene, cyclohexane and toluene or inert gases such as nitrogen and carbon dioxide may also be allowed to coexist as a diluent gas.

The reaction in carrying out the present invention will be explained.

The starting material cyclohexanone oxime is subjected to the catalytic reaction in the gas form. The reaction is carried out in either a fixed-bed or fluidized bed. The nitrogen-containing compounds may be mixed or not with cyclohexanone oxime before they are fed to a reactor. When the nitrogen-containing compounds are not mixed with cyclohexanone oxime before feeding, the nitrogen-containing compounds may be fed in portions. In the case of the fixed-bed reaction, it is preferred to pass a thorough mixture of the cyclohexanone oxime and the nitrogen-containing compounds through the catalyst bed.

Space velocity of the starting material cyclohexanone oxime is usually WHSV=0.1–40 hr$^{-1}$ (namely, feeding rate of cyclohexanone oxime per kg of the catalyst is 0.1–40 kg/hr), preferably 0.2–20 hr$^{-1}$, more preferably 0.5–10 hr$^{-1}$.

Reaction temperature is usually 250°–500° C., preferably 300°–450° C., more preferably 300°–400° C. When the temperature is lower than 250° C., reaction rate is not sufficient and selectivity of ε-caprolactam tends to decrease and when it is higher than 500° C., selectivity of ε-caprolactam tends to decrease.

The present process is carried out under pressure, atmospheric pressure or reduced pressure, but is usually carried out under a pressure of 0.05–10 kg/cm$^2$.

Isolation of ε-caprolactam from the reaction mixture and purification thereof are carried out, for example, by cooling and condensing the reaction product gas, followed by extraction, distillation or crystallization.

Ammonia and methylamines added to the reaction system are separated and recovered from the reaction product and reused. For example, ammonia and methylamines are recovered in a gaseous state in cooling and condensing the reaction product gas.

The catalyst having small activity which is caused by use for long time is easily reactivated to the initial capacity by being calcined in a molecular oxygen-containing gas, for example, air stream or a molecular oxygen-containing gas to which alcohols such as methanol are added. The reactivated catalyst is repeatedly used.

According to the present invention, ε-caprolactam is obtained with high selectivity anti life of tile catalysts is greatly prolonged even under such conditions that cyclohexanon oxime reacts with high conversion.

The following nonlimiting examples will illustrate the present invention.

REFERENCE EXAMPLE 1 (PREPARATION OF CATALYST)

In a stainless steel autoclave (1.5 l) were charged tetraethylorthosilicate ($Si(OC_2H_5)_4$, 100 g, Al content: less than 10 ppm), 10% aqueous tetra-n-propylammonium hydroxide solution (224.0 g) and ethanol (214 g) and were vigorously stirred for 30 minutes. The mixed solution had a pH of 13. The autoclave was sealed and then was dipped in an oil bath to keep the internal temperature at 105° C. Hydrothezmal synthesis was effected for 120 hours with stirring at a revolution rate at least 400 rpm. Pressure in the autoclave reached 2-3 kg/cm². pH at the completion of the hydrothermal synthesis was 11.8. A white solid product was filtered off and washed continuously with distilled water until pH of filtrate reached about 7. The white solid was dried and calcined in an air stream at 500°-530° C. for 4 hours to obtain powdery white crystals (27 g) which were identified to be pentasil type zeolite by powder X-ray diffraction. Al content was 3 ppm according to atomic absorption spectroscopy assay.

To this crystals (10 g) was added 5% aqueous ammonium chloride solution (100 g) to carry out an ion exchange treatment at 50°-60° C. for 1 hour. The crystals were filtered off. The ion exchange treatment was carried out four times and then the crystals were washed with distilled water until no $Cl^-$ ion was detected in the filtrate. Subsequently, the crystals were dried at 120° C. for 16 hours. The resulting crystals of ammonium salt form were shaped under pressure and sifted to obtain particles of 24-48 meshes, which were calcined at 500° C. for 1 hour in a nitrogen gas stream to obtain a catalyst.

REFERENCE EXAMPLE 2 (TREATMENT OF CATALYST)

In a quartz glass reaction tube was packed the catalyst (1 g) prepared in Reference Example 1 and was preheated at 500° C. for 3 hours in a nitrogen stream (4.2 l/hr). Then, the temperature was lowered to 100° C. and the nitrogen gas was replaced with a mixed gas (4.2 l/hr) of nitrogen (95 vol %)-ammonia (5 vol %) and the catalyst was kept at that state for 10 hours. Thereafter, the mixed gas was again replaced with nitrogen (4.2 l/hr) and the temperature was elevated up to 350° C. at a rate of 1° C./min and this temperature was kept for 1 hour, followed by cooling to room temperature with feeding nitrogen.

EXAMPLE 1

In a quartz glass reaction tube (1 cm inner diameter) was packed the catalyst (0.375 g, 0.6 ml) prepared in Reference Example 1 and was preheated in a nitrogen gas stream (4.2 l/hr) at 350° C. for 1 hour. Then, the nitrogen gas was replaced with a mixed gas (4.2 l/hr) of nitrogen (95 vol %)-ammonia (5 vol %).

Then, to the reaction tube was fed a mixed solution of cyclohexanone oxime/methanol (1/1.8 in weight ratio) at a rate of 8.4 g/hr under feeding the above mixed gas to carry out a reaction. At this time, the space velocity WHSV of cyclohexanone oxime was 8 hr$^{-1}$ and temperature of the catalyst bed (reaction temperature) was 350° C. After the reaction was allowed to proceed for 6.25 hours, feeding of all materials was stopped to terminate the reaction. The reaction product was trapped and collected under water cooling and was analyzed by gas chromatography.

The space velocity WHSV of cyclohexanone oxime, the conversion of cyclohexanone oxime and the selectivity of ε-caprolactam were calculated by the following formulas.

WHSV (hr$^{-1}$)=O/C

Conversion of cyclohexanone oxime
(%)=[(X−Y)/X]×100

Selectivity of ε-caprolactam (%)=[Z/(X−Y)]×100 wherein
O=Feeding rate (kg/hr) of cyclohexanone oxime,
C=Weight of catalyst (kg),
X=Mole number of the fed cyclohexanone oxime,
Y=Mole number of unaltered cyclohexanone oxime and
Z=Mole number of ε-caprolactam in the product.

After the reaction was over, the catalyst bed was heated to 430° C. under feeding to the reaction tube a mixed gas of nitrogen, air and methanol (methanol concentration 3.8 vol %: saturated concentration at 0° C.) obtained by bubbling a mixed gas of nitrogen gas (2.5 l/hr) and air (2.5 l/hr) in methanol kept at 0° C. The catalyst bed was treated at that temperature for 23 hours, thereby to remove carbonaceous materials formed on the catalyst.

Then, the temperature was lowered to 350° C. under feeding nitrogen gas (4.2 l/hr). Successively, the reaction and the removal of carbonaceous materials were repeated totally 30 times under the same conditions as above. The results at each time are shown in Table 1.

TABLE 1

| Number of repetition | | Elapsed time of reaction (hr) | | |
|---|---|---|---|---|
| | | 1.25 | 3.25 | 6.25 |
| 1st time | Conversion (%) | 97.7 | 96.6 | 95.5 |
| | Selectivity (%) | 95.7 | 96.3 | 95.7 |
| 2nd time | Conversion (%) | 97.0 | 95.1 | 93.8 |
| | Selectivity (%) | 95.9 | 96.2 | 96.2 |
| 10th time | Conversion (%) | 89.9 | 85.7 | 82.9 |
| | Selectivity (%) | 95.4 | 95.5 | 95.2 |
| 20th time | Conversion (%) | 87.0 | 81.9 | 77.9 |
| | Selectivity (%) | 94.0 | 94.0 | 94.3 |
| 30th time | Conversion (%) | 84.0 | 78.4 | 74.9 |
| | Selectivity (%) | 94.7 | 94.9 | 94.9 |

COMPARATIVE EXAMPLE 1

Reaction and removal of carbonaceous materials were carried out totally 30 times under the same conditions as in Example 1 except that the replacement of nitrogen with the mixed gas of nitrogen-ammonia was not effected. Results of reaction at each time are shown in Table 2.

TABLE 2

| Number of repetition | | Elapsed time of reaction (hr) | | |
|---|---|---|---|---|
| | | 1.25 | 3.25 | 6.25 |
| 1st time | Conversion (%) | 98.0 | 98.6 | 97.6 |
| | Selectivity (%) | 96.1 | 96.2 | 96.7 |
| 2nd | Conversion (%) | 99.3 | 97.9 | 97.1 |

TABLE 2-continued

| Number of repetition | | Elapsed time of reaction (hr) | | |
|---|---|---|---|---|
| | | 1.25 | 3.25 | 6.25 |
| time | Selectivity (%) | 95.2 | 95.4 | 95.2 |
| 10th | Conversion (%) | 95.7 | 91.5 | 89.1 |
| time | Selectivity (%) | 93.3 | 93.4 | 92.8 |
| 20th | Conversion (%) | 88.9 | 81.5 | 77.3 |
| time | Selectivity (%) | 91.3 | 91.7 | 91.6 |
| 30th | Conversion (%) | 83.6 | 74.5 | 68.6 |
| time | Selectivity (%) | 90.8 | 90.9 | 90.8 |

EXAMPLE 2

In a quartz glass reaction tube (1 cm inner diameter) was packed the catalyst (0.375 g, 0.6 ml) prepared in Reference Example 1 and was preheated in a nitrogen gas stream (4.2 l/hr) at 350° C. for 1 hour. Then, the nitrogen gas was replaced with a mixed gas (4.2 l/hr) of nitrogen (95 vol %) -trimethylamine (5 vol %).

Then, to the reaction tube were separately but simultaneously fed a mixed solution of cyclohexanone oxime/methanol (1/1.2 in weight ratio) at a rate of 6.6 g/hr and methanol at a rate of 1.8 g/hr under feeding the above mixed gas to carry out a reaction. At this time, the space velocity WHSV of cyclohexanone oxime was 8 hr$^{-1}$ and temperature of the catalyst bed (reaction temperature) was 350° C. After the reaction was allowed to proceed for 45.25 hours, feeding of all materials was stopped to terminate the reaction. The reaction product was trapped and collected under water cooling and was analyzed by gas chromatography.

Carbonaceous materials formed on the catalyst were removed in the same manner as in Example 1 except that the treating time was 96 hours in place of 23 hours.

Then, the temperature was lowered to 350° C. under feeding nitrogen gas (4.2 l/hr). Successively, the reaction and the removal of carbonaceous materials were repeated totally three times under the same conditions as above. The results at each time are shown in Table 3.

TABLE 3

| Number of repetition | | Elapsed time of reaction (hr) | | | | |
|---|---|---|---|---|---|---|
| | | 1.25 | 13.25 | 25.25 | 37.25 | 45.25 |
| 1st | Conversion (%) | 99.3 | 97.6 | 96.3 | 95.4 | 94.5 |
| time | Selectivity (%) | 95.5 | 95.6 | 96.1 | 96.1 | 96.2 |
| 2nd | Conversion (%) | 98.9 | 97.3 | 96.2 | 95.0 | 94.3 |
| time | Selectivity (%) | 95.8 | 96.2 | 96.1 | 96.1 | 96.1 |
| 3rd | Conversion (%) | 99.5 | 98.7 | 97.7 | 97.0 | 96.2 |
| time | Selectivity (%) | 95.8 | 96.2 | 96.3 | 96.3 | 96.1 |

EXAMPLE 3

In a quartz glass reaction tube (1 cm inner diameter) was packed the catalyst (0.375 g, 0.6 ml) prepared in Reference Example 1 and was preheated in a nitrogen gas stream (4.2 l/hr) at 350° C. for 1 hour. Then, to the reaction tube were separately but simultaneously fed a mixed solution of cyclohexanone oxime/methanol (1/1.2 in weight ratio) at a rate of 6.6 g/hr and a mixed solution of ε-caprolactam/methanol (½ in weight ratio) at a rate of 2.7 g/hr under feeding nitrogen gas (4.0 l/hr) to carry out a reaction. At this time, the space velocity WHSV of cyclohexanone oxime was 8 hr$^{-1}$ and temperature of the catalyst bed (reaction temperature) was 350° C. After the reaction was allowed to proceed for 45.25 hours, feeding of all materials was stopped to terminate the reaction. The reaction product was trapped and collected under water cooling and was analyzed by gas chromatography.

Conversion of cyclohexanone oxime and the selectivity of ε-caprolactam were calculated by the following formulas.

Conversion of cyclohexanone oxime
$$(\%) = [(X-Y)/X] \times 100$$

Selectivity of ε-caprolactam
$$(\%) = [(Z-F)/(X-Y)] \times 100$$

wherein

X=Mole number of the fed cyclohexanone oxime,
Y=Mole number of unaltered cyclohexanone oxime,
Z=Mole number of ε-caprolactam in the product and
F=Mole number of ε-caprolactam fed to the reaction system.

After the reaction was over, carbonaceous materials formed on the catalyst were removed in the same manner as in Example 1 except that the treating time was 96 hours in place of 23 hours.

Then, the temperature was lowered to 350° C. under feeding nitrogen gas (4.2 l/hr). Successively, the reaction and the removal of carbonaceous materials were repeated totally four times under the same conditions as above. The results at each time are shown in Table 4.

TABLE 4

| Number of repetition | | Elapsed time of reaction (hr) | | | | |
|---|---|---|---|---|---|---|
| | | 1.25 | 13.25 | 25.25 | 37.25 | 45.25 |
| 1st | Conversion (%) | 99.6 | 97.7 | 96.3 | 93.7 | 91.8 |
| time | Selectivity (%) | 95.7 | 96.1 | 95.5 | 94.7 | 93.1 |
| 2nd | Conversion (%) | 99.9 | 99.0 | 98.1 | 97.6 | 97.2 |
| time | Selectivity (%) | 96.4 | 96.4 | 96.6 | 95.6 | 94.6 |
| 3rd | Conversion (%) | 99.7 | 98.5 | 97.4 | 96.8 | 95.4 |
| time | Selectivity (%) | 96.0 | 96.2 | 96.3 | 95.7 | 96.1 |
| 4th | Conversion (%) | 99.6 | 98.1 | 97.0 | 95.5 | 95.7 |
| time | Selectivity (%) | 96.3 | 96.5 | 95.8 | 95.4 | 94.8 |

COMPARATIVE EXAMPLE 2

In a quartz glass reaction tube (1 cm inner diameter) was packed the catalyst (0.375 g, 0.6 ml) prepared in Reference Example 1 and was preheated in a nitrogen gas stream (4.2 l/hr) at 350° C. for 1 hour. Then, to the reaction tube were separately but simultaneously fed a mixed solution of cyclohexanone oxime/methanol (1/1.2 in weight ratio) at a rate of 6.6 g/hr and methanol at a rate of 1.8 g/hr under feeding nitrogen gas (4.2 l/hr) to carry out a reaction. At this time, the space velocity WHSV of cyclohexanone oxime was 8 hr$^{-1}$ and temperature of the catalyst bed (reaction temperature) was 350° C. After the reaction was allowed to proceed for 45.25 hours, feeding of all materials was stopped to terminate the reaction. The reaction product was trapped and collected under water cooling and was analyzed by gas chromatography.

After the reaction was over, carbonaceous materials formed on the catalyst were removed in the same manner as in Example 1 except that the treating time was 96 hours in place of 23 hours.

Then, the temperature was lowered to 350° C. under feeding nitrogen gas (4.2 l/hr). Successively, the reaction and the removal of carbonaceous materials were repeated totally four times under the same conditions as above. The results at each time are shown in Table 5.

TABLE 5

| Number of repetition | | Elapsed time of reaction (hr) | | | | |
|---|---|---|---|---|---|---|
| | | 1.25 | 13.25 | 25.25 | 37.25 | 45.25 |
| 1st | Conversion (%) | 99.7 | 98.8 | 97.5 | 97.0 | 94.9 |
| time | Selectivity (%) | 94.4 | 94.9 | 95.1 | 95.1 | 95.0 |
| 2nd | Conversion (%) | 98.2 | 97.0 | 95.1 | 92.2 | 90.5 |
| time | Selectivity (%) | 94.2 | 94.4 | 94.3 | 95.0 | 94.6 |
| 3rd | Conversion (%) | 96.5 | 93.2 | 90.7 | 88.9 | 86.2 |
| time | Selectivity (%) | 93.9 | 94.6 | 94.2 | 94.8 | 94.4 |
| 4th | Conversion (%) | 94.5 | 88.1 | 85.4 | 82.7 | 80.0 |
| time | Selectivity (%) | 94.0 | 94.6 | 94.0 | 94.5 | 94.9 |

COMPARATIVE EXAMPLE 3

The reaction and the removal of carbonaceous materials were repeated totally 30 times under the same conditions as in Comparative Example 1 except that the catalyst (0.375 g, 0.6 ml) treated in Reference Example 2 was packed in a quartz glass reaction tube (1 cm inner diameter) in place of the catalyst prepared in Reference Example 1. Results at each time are shown in Table 6.

TABLE 6

| Number of repetition | | Elapsed time of reaction (hr) | | |
|---|---|---|---|---|
| | | 1.25 | 3.25 | 6.25 |
| 1st | Conversion (%) | 97.9 | 97.5 | 96.9 |
| time | Selectivity (%) | 95.1 | 96.4 | 95.9 |
| 2nd | Conversion (%) | 97.9 | 97.4 | 96.5 |
| time | Selectivity (%) | 94.6 | 94.2 | 93.8 |
| 10th | Conversion (%) | 94.3 | 91.3 | 88.9 |
| time | Selectivity (%) | 92.9 | 93.0 | 93.0 |
| 20th | Conversion (%) | 87.2 | 82.1 | 77.6 |
| time | Selectivity (%) | 91.5 | 92.0 | 91.9 |
| 30th | Conversion (%) | 83.1 | 75.2 | 69.1 |
| time | Selectivity (%) | 90.6 | 90.8 | 91.0 |

What is claimed is:

1. A process for producing ε-caprolactam, which process comprises:
   bringing cyclohexanone oxime, in a gas phase, into contact with a solid catalyst in the presence of at least one nitrogen-containing compound selected from the group consisting of ammonia, methylamines and ε-caprolactam.

2. A process accoridng to claim 1, wherein the solid catalyst is zeolite.

3. A process accoridng to claim 2, wherein the zeolite is a crystalline metallosilicate.

4. A process accoridng to claim 3, wherein the crystalline metallosilicate has a Si/metal atomic ratio of 5 or more.

5. A process according to claim 4, wherein the metal is at least one element selected from Al, Ga, Fe, B, Zn, Cr, Be, Co, La, Ge, Ti, Zr, Hf, V, Ni, Sb, Bi, Cu and Nb.

6. A process accoridng to claim 2, wherein the zeolite is a crystalline silica.

7. A process according to claim 2, wherein the zeolite has a pentasil type structure.

8. A process accoridng to claim 1, wherein amount of the nitrogen-containing compounds is 10 moles or less per mole of the cyclohexanone oxime.

9. A process accoridng to claim 1, wherein a compound represented by the formula (1): $R_1$—O—$R_2$ wherein $R_1$ represents a lower alkyl group which may be substituted with at least one fluorine atom and $R_2$ represents a hydrogen atom, or a lower alkyl or phenyl group which may be substituted with at least one fluorine atom is allowed to exist in the reaction system.

10. A process accoridng to claim 9, wherein the compound represented by the formula (1) is an alcohol of 6 or less carbon atoms.

11. A process accoridng to claim 10, wherein the alcohol of 6 or less carbon atoms is at least one selected from methanol and ethanol.

12. A process according to claim 1, wherein reaction temperature is 250°–500° C.

13. A process accoridng to claim 1, wherein reaction pressure is 0.05–10 kg/cm$^2$.

14. A process accoridng to claim 1, wherein space velocity of cyclohexanone oxime is 0.1–40 hr$^{-1}$.

15. A process accoridng to claim 1, wherein the zeolite catalyst having small activity which is caused by use for long time is activated by being calcined in a molecular oxygen-containing gas.

16. A process accoridng to claim 15, wherein the molecular oxygen-containing gas is air.

17. A process accoridng to claim 15, wherein the molecular oxygen-containing gas contains alcohols.

18. A process according to claim 17, wherein the alcohol is methanol.

* * * * *